United States Patent
Kesaniemi

(10) Patent No.: US 10,806,399 B2
(45) Date of Patent: Oct. 20, 2020

(54) METHOD AND SYSTEM OF MEASURING PATIENT POSITION

(71) Applicant: General Electric Company, Schenectady, NY (US)

(72) Inventor: Martti Ilmari Kesaniemi, Helsinki (FI)

(73) Assignee: General Electric Company, Schenectady, NY (US)

( * ) Notice: Subject to any disclaimer, the term of this patent is extended or adjusted under 35 U.S.C. 154(b) by 452 days.

(21) Appl. No.: 15/359,198

(22) Filed: Nov. 22, 2016

(65) Prior Publication Data

US 2018/0140229 A1    May 24, 2018

(51) Int. Cl.
*A61B 5/00* (2006.01)
*A61B 5/11* (2006.01)
(Continued)

(52) U.S. Cl.
CPC ............ *A61B 5/6823* (2013.01); *A61B 5/055* (2013.01); *A61B 5/1113* (2013.01);
(Continued)

(58) Field of Classification Search
CPC .......... A61B 5/6823; A61B 2562/0219; A61B 2560/0266; A61B 5/1071; A61B 5/704; A61B 5/11; A61B 5/1114; A61B 5/1115; A61B 5/1116; A61B 5/1117; A61B 5/1118; A61B 5/112; A61B 5/1124; A61B 5/1126; A61B 5/113; A61B 5/1135;
(Continued)

(56) References Cited

U.S. PATENT DOCUMENTS

| | | | |
|---|---|---|---|
| 5,697,374 A | 12/1997 | Odagiri et al. | |
| 9,028,407 B1 | 5/2015 | Bennett-Guerrero | |
| 9,095,316 B2 | 8/2015 | Welch et al. | |
| 9,895,086 B2 * | 2/2018 | Van De Laar | ........ A61B 5/1116 |

(Continued)

FOREIGN PATENT DOCUMENTS

| | | |
|---|---|---|
| EP | 1 970 005 A1 | 9/2008 |
| EP | 2 654 030 A1 | 10/2013 |

(Continued)

OTHER PUBLICATIONS

International Search Report and Written Opinion issued in connection with corresponding PCT Application No. PCT/US2017/061755 dated Feb. 26, 2018.

*Primary Examiner* — David J. McCrosky
(74) *Attorney, Agent, or Firm* — Andrus Intellectual Property Law, LLP

(57) ABSTRACT

A method of measuring patient position by a patient monitoring system includes providing a first position sensor attachable to a portion of the patient, and providing a hub device that includes a calibration position sensor. A first calibration position measurement is received from the calibration position sensor while the hub device is aligned with the portion of the patient where the first position sensor is attached. A first patient position measurement is received from the first position sensor, and then a calibration map is determined for the first position sensor based on a difference between the first calibration position measurement and the first patient position measurement. Position measurement data is then received from the first position sensor, and a patient position is determined based on the position measurement data and the calibration map.

19 Claims, 6 Drawing Sheets

(51) Int. Cl.
*A61B 5/113* (2006.01)
*A61B 5/055* (2006.01)
*A61B 5/107* (2006.01)

(52) U.S. Cl.
CPC ............ *A61B 5/1135* (2013.01); *A61B 5/686* (2013.01); *A61B 5/6828* (2013.01); *A61B 5/1071* (2013.01); *A61B 5/1114* (2013.01); *A61B 5/1116* (2013.01); *A61B 2560/0223* (2013.01); *A61B 2560/0242* (2013.01); *A61B 2560/0266* (2013.01); *A61B 2562/0219* (2013.01)

(58) Field of Classification Search
CPC .... A61B 2560/0223; A61B 2560/0228; A61B 2560/0233; A61B 2560/0238
See application file for complete search history.

(56) References Cited

U.S. PATENT DOCUMENTS

| | | | |
|---|---|---|---|
| 2008/0285805 A1* | 11/2008 | Luinge | A61B 5/1114 382/107 |
| 2012/0029300 A1 | 2/2012 | Paquet | |
| 2013/0116602 A1* | 5/2013 | Van Den Heuvel | A61B 5/1116 600/595 |
| 2014/0303524 A1* | 10/2014 | Chen | A61B 5/11 600/595 |
| 2014/0316192 A1* | 10/2014 | de Zambotti | A61B 5/02055 600/28 |
| 2016/0015972 A1 | 1/2016 | Hyde et al. | |

FOREIGN PATENT DOCUMENTS

| | | | | |
|---|---|---|---|---|
| EP | 2832289 A1 | 2/2015 | | |
| WO | 2008/155693 A1 | 12/2008 | | |
| WO | WO-2008155693 A1 * | 12/2008 | ........... | A61B 5/1116 |

* cited by examiner

METHOD AND SYSTEM OF MEASURING PATIENT POSITION

BACKGROUND

The present disclosure generally relates to patient medical monitoring systems, and more specifically to patient monitoring systems capable of monitoring patient position and the calibration of such patient position measurement within a patient monitoring system.

Patient monitors for monitoring physiological data of a patient often comprise a central hub connectable, either by wired or wireless means, to multiple auxiliary devices that acquire physiological data from the patient. Thereby, multiple different types of physiological data are acquired by multiple different data acquisition devices, which transmit the physiological data to the hub device. The hub device may then process the physiological data and/or transmit the physiological data to a central network for storage in a patient's electronic medical record. The hub device may also include or be in communication with a display to display the physiological data to a clinician. The hub device may be connectable by wired or wireless means to one or more of several different physiological data acquisition devices simultaneously, which may include but are not limited to a pulse oximeter (SPO2), a non-invasive blood pressure monitor (NIBP), an end-title CO2 (EtCO2) monitor, an electrocardiograph (ECG) device, an electroencephalograph (EEG) device, a temperature monitor, an invasive blood pressure monitor, a capnograph, a respiration monitor, or the like.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of measuring patient position by a patient monitoring system includes providing a first position sensor attachable to a portion of the patient, and providing a hub device that includes a calibration position sensor. A first calibration position measurement is received from the calibration position sensor while the hub device is aligned with the portion of the patient where the first position sensor is attached. A first patient position measurement is received from the first position sensor, and then a calibration map is determined for the first position sensor based on a difference between the first calibration position measurement and the first patient position measurement. Position measurement data is then received from the first position sensor, and a patient position 34 is determined based on the position measurement data and the calibration map.

A patient monitoring system includes a first position sensor attachable to a portion of the patient, a hub device including a calibration position sensor, a processor, and a position analysis module executable on the processor. The position analysis module is executable to receive a first calibration position measurement from the calibration position sensor while the hub device is aligned with the portion of the patient where the first position sensor is attached, and to receive a first patient position measurement from the first position sensor. The position analysis module determines a calibration map for the first position sensor based on the difference between the first calibration position measurement and the first patient position measurement.

A method of calibrating position measurement by a patient monitoring system includes attaching a first position sensor to a patient and providing an input command via a user interface associated with the hub device to record a first calibration position measurement. The first calibration position measurement is then recorded from the data provided by the calibration position sensor. A first patient position measurement is recorded from the data provided by the first position sensor, and then a calibration map is determined for the first position sensor based on a comparison between the first calibration position measurement and the first patient position measurement.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
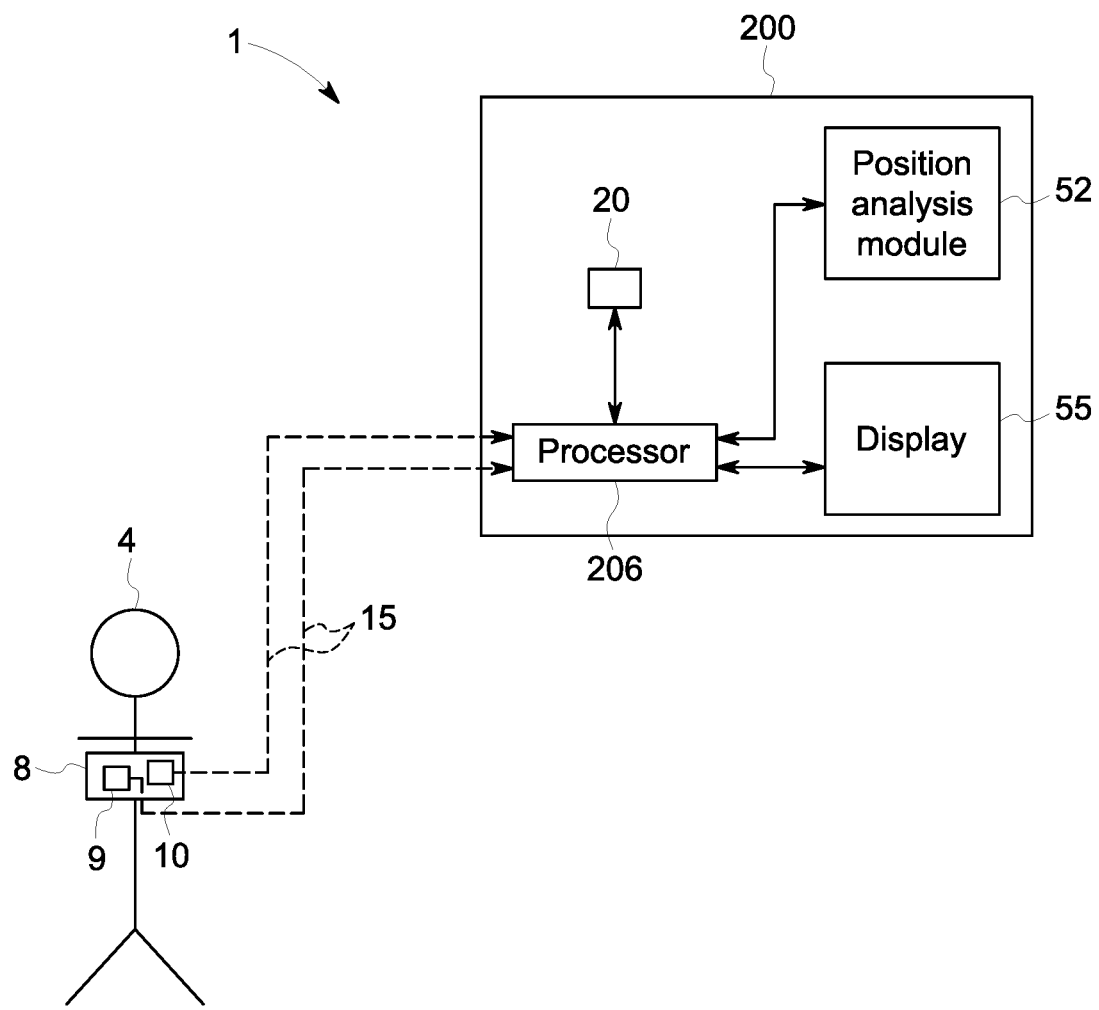
FIG. 1 is a schematic diagram of one embodiment of a patient monitoring system that measures patient position.

The present disclosure was developed in view of the inventor's recognition of the value of patient position monitoring as part of an overall patient monitoring system. For example, patient position monitoring can be used to supplement and interpret physiological information gathered by other patient data acquisition devices, it can be used as a control function for controlling different aspects of the system, or it can be used as a patient monitoring element on its own. To provide just a few examples, patient position information can be used to interpret or check physiological information gathered from other devices. For example, if a patient is determined to be walking, the system may be relatively certain that a patient is not experiencing a critical medical event, such as a heart attack, and thus may disregard certain alarm conditions as being caused by noise, detachment of sensors, etc. Likewise, the system may adjust thresholds for various physiological data assessments based on the patient activity. Alternatively or additionally, the system may control monitoring functions based on patient position, such as to turn off certain monitoring functions when the patient position is not conducive for obtaining reliable data. For example, the system may prevent a non-invasive blood pressure measurement by an NIBP monitor within the system while the patient is walking or otherwise moving, as non-invasive blood pressure monitoring consumes significant energy and is likely to be unreliable if the patient is moving. Thereby, a wireless monitoring system may optimize battery life and obtain the most reliable data based on patient position. Finally, the inventor has also recognized that patient position may provide an additional physiological monitoring element within the monitoring system. For example, the patient monitoring system can operate to notify a clinician if a patient has been in the same position for too long to help avoid complications due to patient immobility.

Through experimentation and research in the relevant field, the inventor has recognized that in wireless monitoring systems where data acquisition devices are variously attached and detached from a patient, a method and system are needed to reliably determine a patient's position and/or activity during monitoring. The inventor has also recognized that the incorporation of position sensors into various body-worn data acquisition devices (or separately attached to a patient) requires calibration of those position sensors so that the position measurement data can be accurately interpreted. Patient's bodies are all different, and it may be difficult or impossible to create a position measurement device that can be attached to every patient in the same way and in a way that allows position measurements that represent patient position to be measured. For instance, patient's chests are all shaped differently, and it will not always be possible to mount a position sensor on a patient's chest in a way that exactly aligns with, or is parallel to, a coordinate system of the patient's chest. For example, the position sensor may be misaligned with the patient's body in any one or more of the vertical, horizontal, or sagittal planes.

Accordingly, the inventor further recognized that such calibration can be provided by incorporating a calibration position sensor within a central monitoring element, such as into a hub device. The hub device is rotated into alignment with the portion of the patient to which the one or more position sensors for patient position monitoring are attached. The calibration position sensor measures the relevant calibration position with respect to a zeroed position, such as a measurement with respect to each of a vertical, horizontal, and sagittal axis. The position measured by the position sensor on the patient at that moment can be compared to the position measured by the calibration position sensor in order to create a calibration map that correlates the two measurements. Thereafter, measurements from the position sensor attached to the patient are interpreted according to the calibration map in order to monitor the patient's position. In certain embodiments, a patient monitoring system may include multiple position sensors attached to the patient, and each position sensor is calibrated to the calibration position sensor according to its own calibration map.

FIG. 1 depicts one embodiment of a patient monitoring system 1 that measures position of the patient 4. The system 1 includes a hub device 200 in communication with, such as by wireless communication means, a data acquisition device 8 that includes a position sensor 10. The data acquisition device 8 may be any of various types of data acquisition devices, and particularly those that may be appropriately attached to the patient's abdomen, chest, shoulder, waste, hip, or the like. For example, the data acquisition device 8 may be attached to the patient 4 by a strap or an adhesive, fixed to the patient's clothing, etc. For instance, the position sensor 10 may be incorporated into a data acquisition device 8 that is a respiratory monitor strapped around the patient's chest, such as a transducer device attached to a patient's thoracic or abdominal area to measure expansion and contraction during respiration. However, a person of ordinary skill in the art will understand in light of this disclosure that the position sensor 10 may be incorporated into any data acquisition device 8 attachable to a portion of the patient 4 that can be used to determine the patient's position.

Alternatively or additionally, the system 1 may include a separate data acquisition device dedicated to patient position sensing and including the position sensor 10 and circuitry necessary for communicating the measurements from the position sensor to the hub device 200. For example, such a patient position acquisition device may include a wireless transmitter for wirelessly communicating the position measurement data to a corresponding wireless transceiver in the hub device 200. The position measurement data measured by the position sensor 10 is communicated from the data acquisition device 8 to the hub device 200 via communication link 15, which may be by any wired or wireless means. For example, a wireless embodiment of the communication link 15 may be according to any of various radio frequency protocols, such as Bluetooth, Bluetooth low energy, ANT, or according to any of various wireless networks protocols, such as on the wireless medical telemetry service (WMTS) spectrum or on a WiFi-compliant wireless local area network (WLAN).

Furthermore, the system may include any number of position sensors 10 to measure the position of the patient 4. Measurements by the position sensors 10 may be continuous or at given intervals. In the embodiment depicted in FIG. 2, for example, the patient monitoring system 1 includes a first position sensor 10a and a second position sensor 10b. Each position sensor 10a, 10b measures position of the portion of the patient's body to which the position sensor is attached, and such position measurement data is communicated to the hub device via communication links 15a and 15b, respectively.

The hub device 200 receives position measurement data from the position sensor(s) 10 and interprets the position measurement data to determine a patient position 34. The system 1 includes a position analysis module 52 that is a set of computer executable instructions that determine the patient position 34 based on the position measurement data from the one or more position sensor(s) 10. The position analysis module 52 may then output the patient position 34, which may be used in various ways by other aspects of the patient monitoring system and/or stored in the patient's medical record.

In the depicted embodiment, the position analysis module 52 is incorporated into the hub device 200, such as stored within memory of a computing system 201 of the hub device 200 (see FIG. 4) and executed on the processor 206 of the computing system 201. In other embodiments, the position analysis module 52 may be incorporated in another portion of the patient monitoring system 1, such as within a central patient monitor networked with the hub device 200.

In order to accurately interpret the position measurement data from the position sensor 10, a calibration exercise is executed by the position analysis module 52, examples of which are described herein. The calibration exercise utilizes a calibration position sensor 20 within the hub device 200. The calibration measurement sensor 20 provides a calibration position measurement of the patient's position, which it measures with respect to its known zeroed position 42, or defined set of coordinate axis locations. In the calibration exercise, position measurement data from the calibration position sensor 20 is compared and correlated to position measurement data gathered from the position sensor 10 while both the position sensor 10 and the calibration position sensor 20 are in approximately the same position—which represents the position of the portion of the patient 4 to which the position sensor 10 being calibrated is attached. As illustrated in FIGS. 3B-3D, the calibration exercise involves rotating the hub device 200 containing the calibration position sensor 20 into alignment with the patient 4, such as the portion of the patient to which the position sensor 10 is attached. The position measurement data 30 from the calibration position sensor 20 is then compared to the position measurement data 30 from the patient position sensor 10 to determine a calibration map which correlates the position measurements from the two sensors. Since the calibration position sensor 20 is calibrated to a known zeroed position 42, the calibration exercise then allows for subsequent position measurement data 30 from the position sensor 10 to be interpreted with respect to the known zeroed position, or set of axes. The position analysist module 52 has a map or matrix of patient positions relative to the zeroed position coordinate system to which the calibration position sensor 20 measures the calibration position measurement, and thus according to which the position sensor 10 is calibrated. The patient's current position is then known with respect to the zeroed axes.

The patient position sensor 10 and the calibration position sensor 20 may include any one or more of an accelerometer, a gyroscope, and a magnetometer. For example, the position sensors 10, 20 may each include a three-axis accelerometer, a three-axis gyroscope, or a combination three-axis accelerometer/gyroscope sensor. In other embodiments, the position sensors 20 may each include a magnetometer to measure the magnetic field, and thus to measure position with respect to the magnetic field. For example, where an accelerometer is used, a magnetometer may also be also used to provide additional information that allows calibration along more axes using fewer calibration steps.

Depending on how the accelerometer is attached to the patient—and thus how many free angles there are between the coordinate system for the calibration position sensor 20 and the coordinates system for the position sensor 10, and depending on how many of those axes are wished to be accurately correlated—calibration between the two position sensors 10 and 20 may require more than one correlation point. Accordingly, a patient may be moved to a second calibration position and the hub device 200 may be moved into alignment with the second calibration position, and then the calibration process is repeated to create a second calibration point. The second calibration point provides additional information that can be used to align the position measurement data from the respective position sensors 10, 20 along additional axes, such as a second and third axes. For example, where the position sensor 10, 20 are three-axis accelerometers, and the patient position sensor 10 is known to be attached to the chest of the patient 4, the patient may be instructed to assume a predetermined position or perform a predetermined motion that causes a known rotation. Two axes of the accelerometer coordinates system will lie on one plane of the coordinates system for the patient position sensor 10. The relative positions within those two axes in that plane will then be known based on the predetermined position or motion instructed for the patient. Alternatively or additionally, the correlation of the respective axes of the patient position sensor 10 and the calibration position sensor 20 may be supplemented or assisted by certain known conditions. For example, if the patient position sensor 10 is attached to the patient in a predefined orientation, e.g., the top side of the device is pointing toward the patient's head, then that information can be used to eliminate certain possible correlation permutations, and thus the correlation between the coordinates of the patient position sensor 10 and the calibration position sensor 20 can be resolved in fewer steps.

Where more accurate calibration between the two coordinate systems is desired, the process can be repeated with several patient orientations that allow identification and correlation of each axis individually. An example of such a process is described below with respect to FIGS. 3A-3D. Alternatively or additionally, each of the position sensors 10 and 20 may incorporate a magnetometer, and thus the calibration map may include correlation between the respective magnetometer coordinate systems. In such an embodiment, a single correlation measurement is enough to determine a full calibration map along all three axes. This requires an assumption that the magnetic field sensed by each respective position sensor 10, 20 are parallel to one another and are different from the direction of the gravitational field. In practice, the magnetic field is seldom perfectly vertical, i.e., parallel to the gravitational field, except near the magnetic poles of the earth. However, medical monitoring environments often are noisy environments for such magnetic measurements, and thus in certain environments it may be beneficial to require that the calibration position sensor 20 be in close proximity with the patient position sensor 10 during the calibration process. This significantly increases the chance of having sufficiently parallel magnetic fields at the two sensor locations.

Accelerometers are often prone to detect the acceleration caused by a moving patient, such as changing position or walking, for example, and these accelerations hide the orientation information of the sensor. Alternatively or in addition to incorporating a gyroscope or a magnetometer in the position sensors 10, 20, multiple position sensors may be utilized to eliminate the ambiguity of the position measurement data 34 caused by the accelerations created through patient movement. If each position sensor 10 is calibrated properly, the patient position 34 may be more accurately determined based on position measurement data 34 from multiple position sensors 10 on the patient 4. For example, the output of each of the multiple position sensors may be compared to find commonalities in sensed position, increasing the likelihood that the output is a measurement of patient position rather than noise. For example, when having an accelerometer positioned to the right-hand side of the patient's chest, if the patient moves his right arm while conducting an activity, such as eating, this sensor is likely to catch the accelerations caused by the hand movement, and the patient orientation becomes ambiguous. In there is another accelerometer attached to the left-hand side of the patient's chest, this accelerometer is less prone to the movement accelerations, and the patient position can be detected by using the signal of the second accelerometer. Further, the problem of such movement "artifacts" or ambiguity may be solved by using a combined gyroscope-accelerometer as the orientation sensor, which allows movement tracking even during motion.

Figure 2:
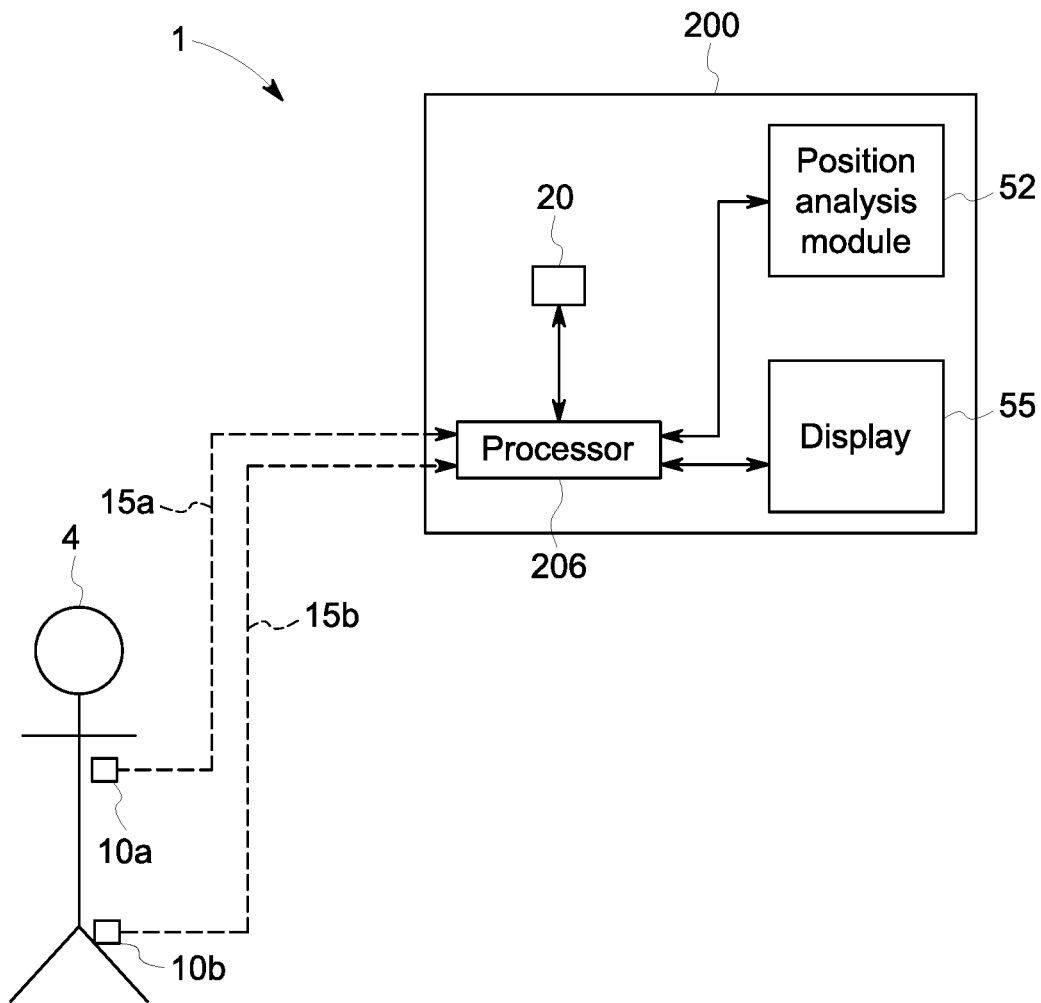
FIG. 2 is a schematic diagram of another embodiment of a patient monitoring system that measures patient position.

In other embodiments were the system includes multiple position sensors 10a, 10b are one or more of the position sensors 10a, 10b may be placed on areas of the patient other than the patient's chest or torso, such as on the patient's arm or legs. This can provide more detailed position information that may be used to precisely define patient positions 34, and thus provide very precise position monitoring. For example, as shown in FIG. 2, a second position sensor 10b may be positioned on the patient's leg, in addition to a position sensor 10a on the patient's chest or torso, in order to allow the system 1 to differentiate between standing and sitting vertical positions. In such an embodiment, the position sensor 10a detects a vertical, upright position when the patient 4 is in both a standing and a seated position. In order to provide information that differentiates between the standing and seated positions, the second position sensor 10b may be placed on the patient's leg, such as on the patient's thigh, which will detect a horizontal position when the patient 4 is seated and a vertical position when the patient 4 is in a standing position.

The calibration process requires alignment of the hub device 200 with the portion of the patient where the calibrated position sensor is attached, thereby to calibrate the position measurement data from the relevant position sensor 10 to the position measured by the calibration position sensor 20. Depending on the make up of the position sensors 10, 20 and the calibration process, multiple patient position sensors 10a, 10b may be calibrated at one time, or each patient position 10a, 10b may need to be calibrated separately.

Figure 3A:
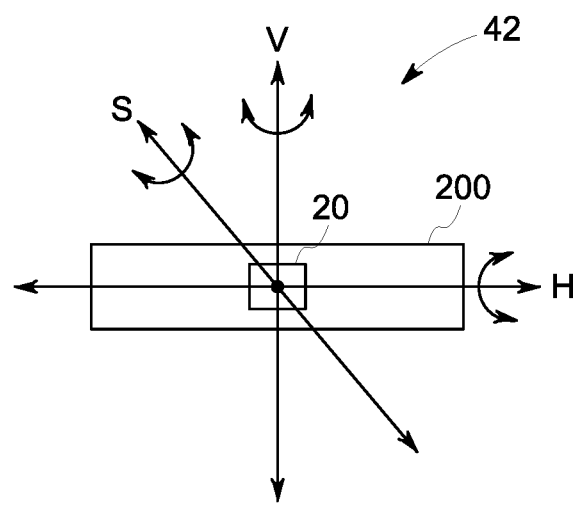
FIG. 3A depicts a hub device having a three-axis position sensor in a zeroed position.
Figure 3B:
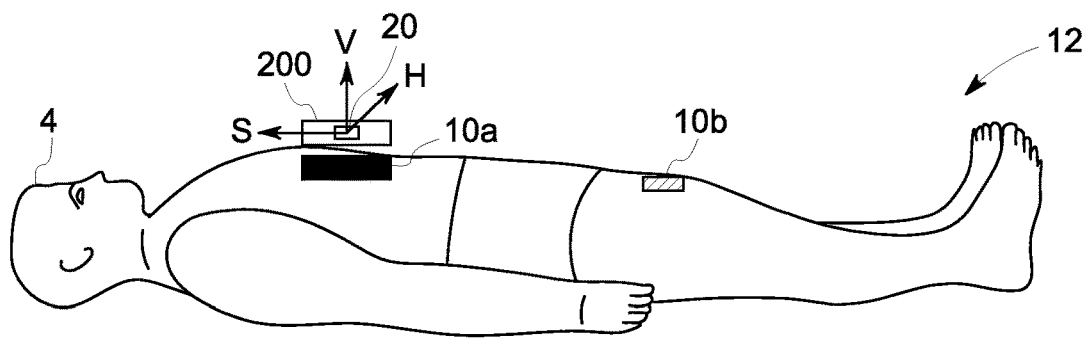
FIGS. 3B-3D depict exemplary steps for calibrating patient position measurement by the patient monitoring system.
Figure 3C:
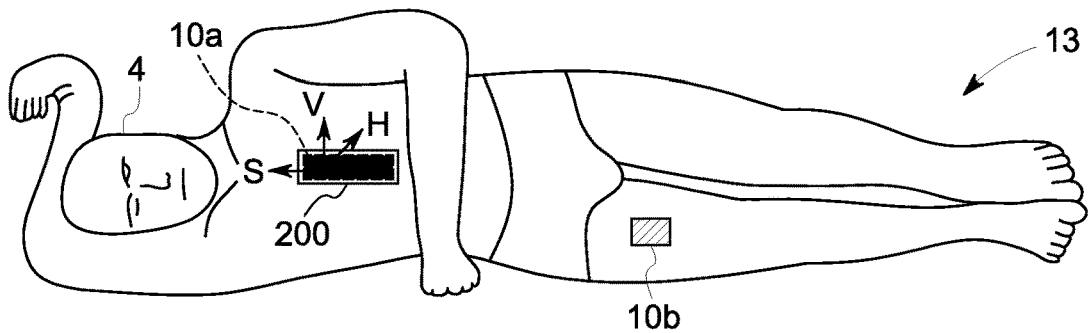
Figure 3D:
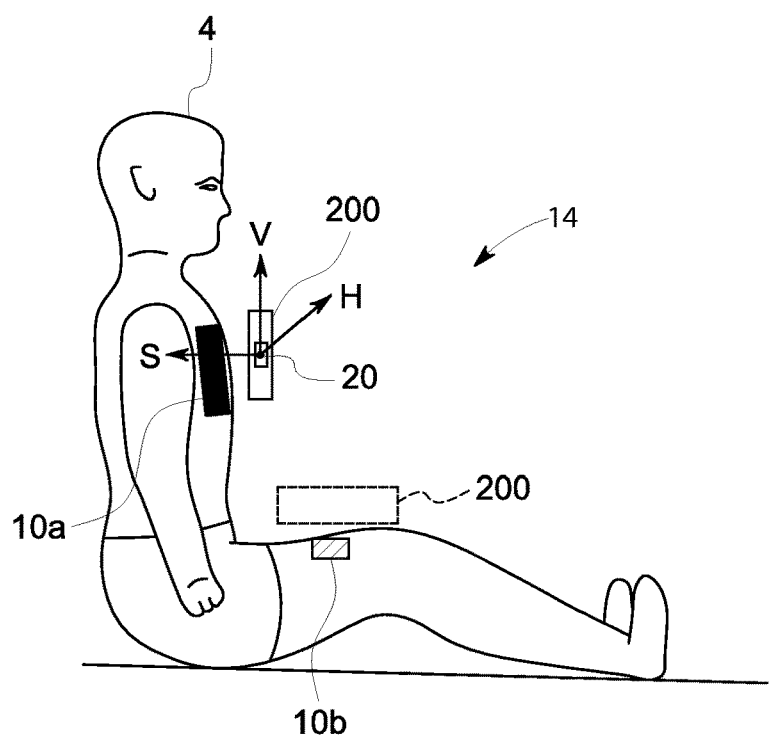

FIG. 3A depicts a hub device 200 having a calibration sensor 20 in a zeroed position 42, where the measurement with respect to a coordinate system of a horizontal axis H, a vertical axis V, and a sagittal axis S are zero. For example, the zeroed position 42 may be calibrated, or determined, when the hub device 200 is laying flat on a table, or in some other predefined position. In an embodiment where the calibration position sensor includes a magnetometer, this step may not be necessary. The hub device is then rotated to be in alignment with the patient position, which could include simply rotating the hub device at its current location or moving the hub device 200 over to the patient 4 and aligning the hub device 200 with the portion of the patient where the position sensor 10 is attached.

FIGS. 3B-3D depict one embodiment of a calibration process where the calibration map is determined based on alignment of the position measurement data from the respective position sensors 10, 20 at three calibration positions. As described above, in certain embodiments calibration can be reached by taking calibration position measurements at only one calibration position, which could be any of the positions depicted in FIGS. 3B-3D, or any other position which might be conducive for calibration.

FIG. 3B depicts a first calibration step where the patient 4 assumes a first calibration position 12, which in the depicted embodiment is exemplified as a supine position. The hub device 200 is aligned with the patient's chest, which is the portion of the patient where the first position sensor 10a is attached. For example, the hub device 200 may be attached to the patient at a location near the position sensor 10, or the hub device 200 could attach to a housing of the device containing the position sensor 10. In such an embodiment, the hub device 200 could be maintained in the same relative position with respect to the position sensor 10 during the calibration process. In other embodiments, the hub device 200 does not remain fixed to the patient 4 during the calibration process, and is simply held in proximity to the patient 4. As described above, in other embodiments where the hub device 200 does not need to be in proximity to the position sensor 10, the calibration process may simply entail remotely rotating the hub device to be in alignment with the relevant portion of the patient 4 having the position sensor 10, which could be done from any remote location.

Once the hub device 200 is rotated into alignment with the portion of the patient containing the position sensor 10, a first calibration position measurement is recorded from the calibration position sensor 20. For example, the first calibration position measurement may be recorded in response to an input command 40 from a clinician via a user interface 210 on the hub device 200, which the clinician inputs once the hub device 200 is properly aligned and measurements should be taken. For example, the input command could be given via Near Field Communication, i.e., the clinician's action of bringing the hub close to the first position sensor could launch the calibration. This might be handy if the first position sensor must be paired with the hub, as then the pairing and calibration could be done in a single step.

A first patient position measurement is also received and recorded from the relevant position sensor 10 for which the calibration is occurring. For example, the data acquisition device 8 may continually transmit position measurement data 30 to the hub device 200. The first patient position measurement is then correlated to the first calibration position measurement by a calibration map. For example, the calibration map can be determined based on a difference with respect to one or more axes between the first calibration position measurement and the first patient position measurement. In certain embodiments, this may be a sufficient calibration process. As explained above, calibration may require measurements at additional calibration positions in order to align the position measurements from the respective sensors along additional axes.

FIG. 3C depicts a second calibration step where a patient assumes a second calibration position 13, which is exemplified as a right side relined position. The calibration positions may be predetermined positions, which can be instructed by the position analysis module 52 as part of the calibration process. Alternatively, the calibration positions may vary, and may be identified and determined by the position analysis module 53 based on the position measurements recorded by the calibration position sensor 20, which are measured with respect to the zeroed position. Once the patient has reached the second calibration position 13 and the hub device 200 is brought into alignment with the relevant portion of the patient containing the position sensor 10 being calibrated, a second calibration position measurement from the calibration position sensor 20 is recorded by the position analysis module 52. Likewise, a second patient position measurement is recorded from the position sensor 10. One or more axes of the coordinates for the position sensor 10 may be determined by comparing the measurement data recorded at the first calibration step and at the second calibration step to resolve the correlation along all three axes. With respect to the example shown in FIGS. 3B and 3C, the axis with the least (possibly zero) change in position measurement would identifiable as the sagittal axis S, because the patient rolls about the sagittal axis in transitioning from the first calibration position 12 to the second calibration position 13. As the patient rotates about the sagittal axis S changes will be seen in both the vertical and horizontal measurement values. As described above, where a magnetometer is present, the vertical axis V may be identified immediately by comparing the magnetic measurement data from the respective position sensors 10, 20. In an embodiment where the position sensor includes both an accelerometer and a magnetometer, all three axes are determined with certainty after a single calibration step.

FIG. 3D exemplifies a third calibration step where the patient assumes a third calibration position 14, which in the depicted example is an upright sitting position. As described above, a third calibration position measurement may be recorded from the calibration position sensor 20, and a third patient position measurement recorded from the position sensor 10 being calibrated. Based on a comparison of the first, second, and third calibration position measurements, all three axes in the coordinate system for the position sensor 10 may be identified with additional certainty and accuracy. However, as described herein, depending on the configuration of the position sensors 10, 20, all three axes may also be identified using only one or two calibration measurements. The calibration map is then determined to map the position measurement values onto the calibration position measurements, thereby creating a map that equates the position measurement data from the position sensor 10 to the position measurement data from the calibration position sensor 20, and will be interpreted by the position analysis module 52 accordingly. Thus, the exact orientation of the calibrated position sensor 10 becomes less important, so long as it stays fixed to the patient in the same position it was in at the time of calibration. For example, differences in the angle at which the position sensor 10 is attached to the patient and the general axis of that portion of the patient's body are accounted for in the calibration process. For example, as shown in FIG. 3D, if the position sensor 10 is attached to a portion of the patient's chest that is not completely parallel with the general axis of the patient's upper body as a whole, that difference will be accounted for in the calibration process so that the position measurement data is accurately mapped to the patient's sitting position.

In the case of two accelerometers, one attached to the patient and the other in the hub device, the calibration measurement can be thought as fixing the patient attitude with an axis that travels through the patient in the same direction as the gravitation field. Thus, with a single measurement and a single three-axis accelerometer sensor, one angle is left unknown: it is the rotation angle around the axis defined by the measured gravitation field. In the case of an accelerometer only, this unknown angle can be solved through moving the patient to another orientation in respect to the gravitation field and then repeating the calibration. After the second calibration measurement, there are two axes fixing the patient position, and there are no more ambiguous angles left.

In the case of position sensors with both an accelerometer and a magnetometer, two axes can be defined with a single measurement: the axis defined by the gravitation field and the one defined by the magnetic field. As the magnetic field typically has some other direction than the gravitation field, these two axes fix the patient position unambiguously, and a full calibration is received with a single measurement. However, even though two measurement vectors are enough to create the calibration map, the effect of possible measurement errors can be reduced by increasing the amount of calibration measurements.

In an embodiment of the patient monitoring system 1 that includes multiple position sensors 10, the position sensors may be calibrated as part of the same calibration process, or may be calibrated using separate calibration steps. With reference to FIGS. 3B and 3C, for example, the position sensors 10a and 10b are generally in the same plane as one another and providing approximately the same position output. Thus, both position sensors 10a and 10b could be calibrated to the calibration position sensor 20 in the same calibration step. For example, in the first calibration step where the patient is in the first calibration position 12 (the supine position), the position sensors 10a and 10b can each be compared to the first calibration position measurement from the calibration position sensor 20. A separate calibration map is thus created for each position sensor 10a, 10b, mapping the first patient position measurement from each of the position sensors 10a, 10b to the same calibration position measurement. Likewise, the same thing can be done when the patient is in the second calibration position 13 (the right side reclined position). Namely, the second patient position measurements from each of the position sensors 10a, 10b are mapped to the second calibration measurement from the calibration sensor 20.

However, separate calibration steps must be performed for the position sensors 10a and 10b where the positions being measured are not in the same plane. As exemplified in FIG. 3D, the first position sensor 10a on the patient's chest measures a vertical patient position, where as the second position sensor 10b on the patient's leg measures a horizontal patient position. Accordingly, separate calibration steps must be performed when the patient is in the seated position, or for any other position where the sensed positions are not redundant. Accordingly, as is depicted in FIG. 3D, the hub device 200 must be separately aligned with the patient's chest and a calibration position measurement recorded and compared to the relevant position measurement from the first position sensor 10a, and then the hub device 200 is rotated into alignment with the patient's leg and another calibration position measurement is recorded and used for comparison to the corresponding patient position measurement from the second position sensor 10b.

In still other embodiments, the calibration may occur based on position measurements taken while the patient is moving. For example, the patient may be instructed to move from the supine position depicted in FIG. 3B to the right side reclined position depicted in FIG. 3C and simultaneous measurements may be recorded from each of the calibration position sensor 20 and the respective position sensor 10 being calibrated. The calibration map can then be determined based on the comparison between the respective measurements from each of the position sensors 10, 20. Alternatively or additionally, the patient 4 may be instructions to move from the supine position depicted in FIG. 3B to the seated position depicted in FIG. 3D, and multiple position measurements may be simultaneously recorded from the position sensor 10 and the calibration sensor 20. The position measurements are then compared to create the calibration map based on a comparison of the respective position measurements, and especially the changes with respect to the horizontal axis H of the respective position measurement data sets.

Figure 4:
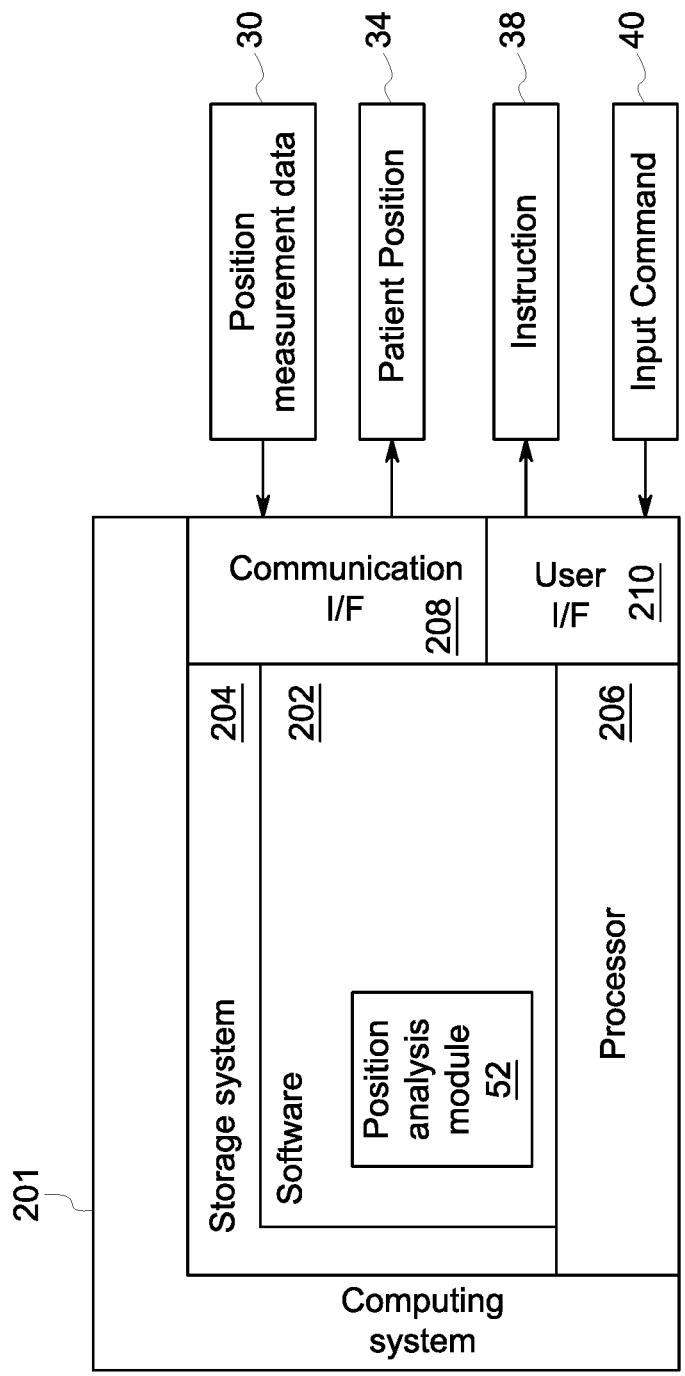
FIG. 4 is a schematic diagram of one embodiment of a computing system in a hub device of a patient monitoring system.

FIG. 4 provides a system diagram of an exemplary embodiment of a computer system 201 in a hub device 200, which incorporates the position analysis module 52. The computing system 201 generally includes a processor 206, storage system 204, software 202, communication interface 208 and a user interface 210. The processor 206 loads and executes software 202 from the storage system 204, including the position analysis module 52, which is an application within the software 202. The module 52 includes computer-readable instructions that, when executed by the computing system 201 (including on the processor 206), direct the processor 206 to operate as described in herein in further detail, including to execute one or more of the steps described.

Although the computing system 201 as depicted in FIG. 4 includes one software element 202 encapsulating one position analysis module 52, it should be understood that one or more software elements having one or more modules may provide the same operation. Thus, the functions described herein as being performed by the position analysis module 52 may be directed and executed by a single software application, or by many separate software applications. Similarly, while description as provided herein refers to a computing system 201 and a processor 206, it is to be recognized that implementations of such systems can be performed using one or more processors, which may be communicatively connected, and such implementations are considered to be within the scope of the description. For example, the processor 206 may encompass a distributed processing system, such as in a cloud computing environment and system.

The processor 206 may comprise a microprocessor and other circuitry that retrieves and executes software 202 from storage system 204. Processor 206 can be implemented within a single processing device, but can also be distributed across multiple processing devices or sub-systems that cooperate in executing program instructions. Examples of processors 206 include general purpose central processing units, application-specific processors or integrated circuits, and logic devices, as well as any other type of processing device, combinations of processing devices, or variations thereof.

The storage system 204, can comprise any storage media, or group of storage media, readable by processing system 206 and/or capable of storing software 202, as well as storing position measurement data 30. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the position measurement data 30. Storage system 204 can further include additional elements, such a controller capable, of communicating with the processor system 206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processing system 206 (such as within a housing of the hub device 200), or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between elements within the computing system 201 and external devices. For example, the communication interface 208 is configured to communicate (such as via wireless communication means) with the data acquisition device 8 to receive the position measurement data 30 from the one or more patient position sensors 10 and the calibration position sensor 20. The user interface 210 may configured to receive input from a clinician, such as an input command 40 instructing recording of a calibration measurement, and to output the instructions 38, such as instructions for the calibration steps. User interface 210 may include a video or graphic display, which may also be a touch screen. The user interface 210 may further include a mouse, a keyboard, a voice input device, a touch input device for receiving a gesture from a user, a motion input device for detecting non-touch gestures and other motions by a user, and other comparable input devices and associated processing elements capable of receiving user input from a user, such as a clinician. Speakers, printers, haptic devices and other types of output devices may also be included in the user interface 210, such as to provide auditory instructions 38 to a clinician on how to perform one or more of the calibration steps.

Figure 5:
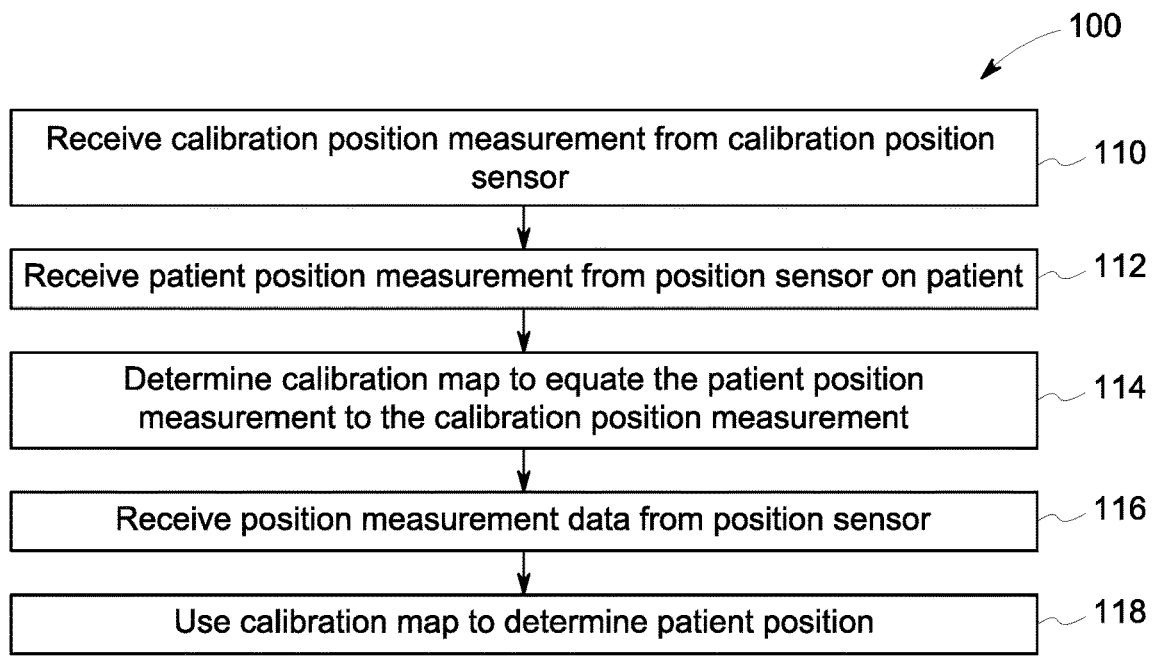
FIG. 5 depicts one embodiment of a method of measuring patient position by a patient monitoring system.
Figure 6:
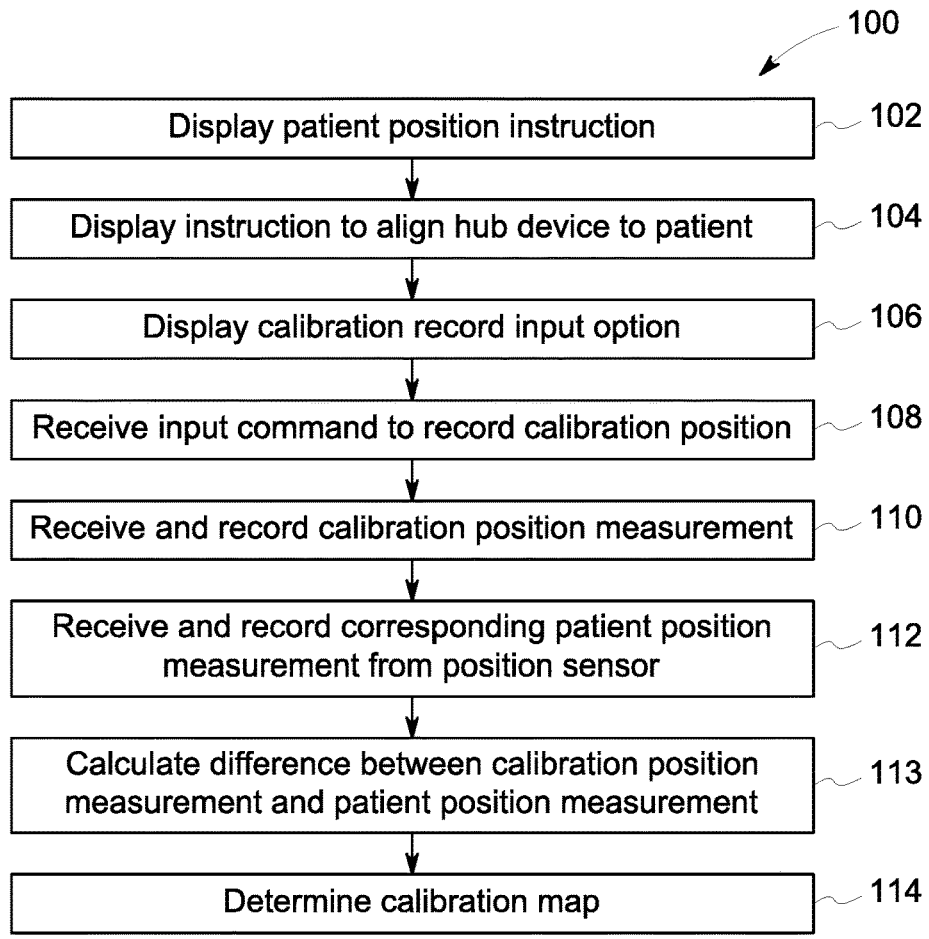
FIG. 6 depicts another embodiment of a calibration portion of a method of monitoring patient position by a patient monitoring system.
Figure 7:
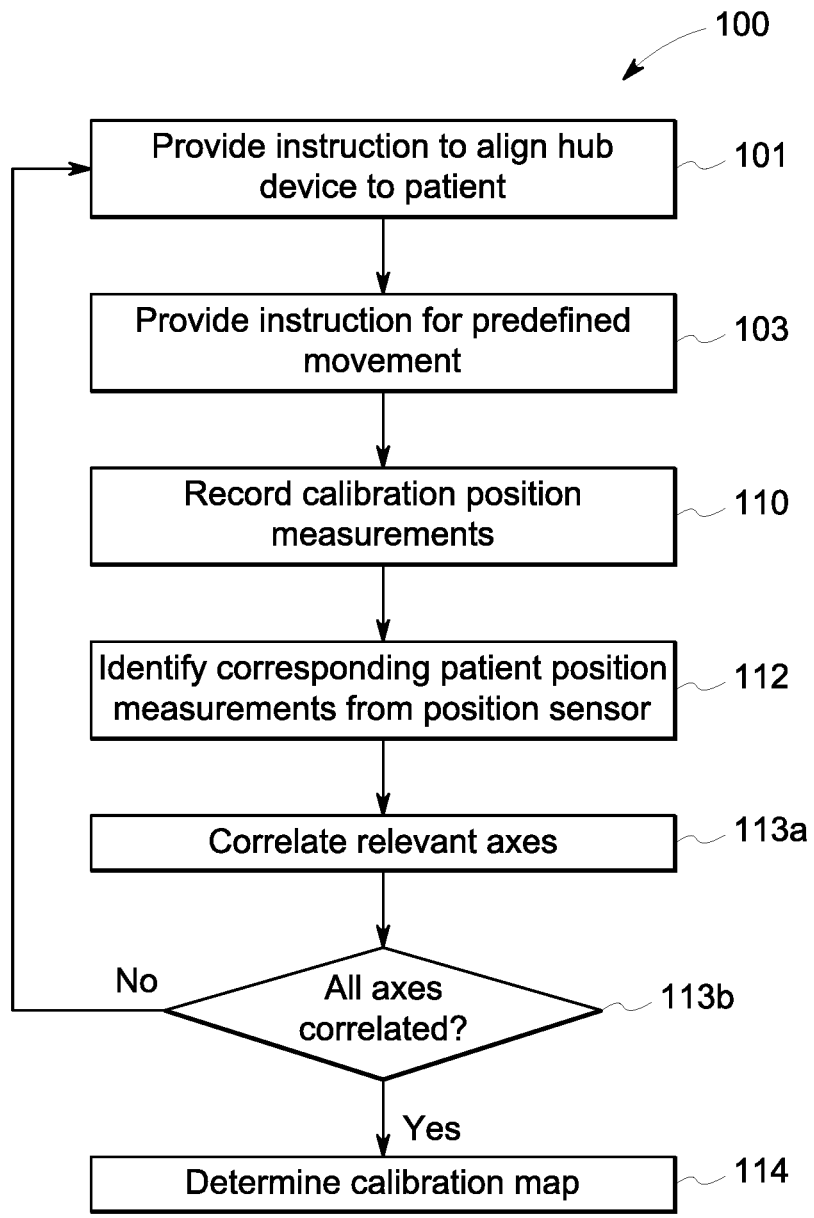
FIG. 7 depicts another embodiment of a calibration portion of a method of measuring patient position by patient monitoring system.

FIGS. 5-7 depict various embodiments of methods 100 of measuring patient position by patient monitoring system, including embodiments of the calibration portion of the method 100. With reference to FIG. 5, a calibration position measurement is received at step 110 from the calibration position sensor 20, and a patient position measurement is received at step 112 from the position sensor 10 being calibrated. Steps are executed at step 114 to determine a calibration map that equates the patient position measurement to the calibration position measurement, and thus can be used to equate future position measurement data 30 received from the position sensor 10 to the coordinate system of the calibration position sensor 20, which is known to the position analysis module 52. Subsequent position measurement data 30 is then received from the calibrated position sensor 10, which is represented at step 116. Steps are then executed at step 118 to determine the patient position 34 from the position measurement data using the calibration map In the embodiment depicted in FIG. 6, a patient position instruction 38 is displayed at step 102, such as on a display 55 of the hub device 200. For example, instruction 38 may be executed to control the display 55 to display a command for the patient to assume a particular calibration position, such as the first calibration position 12. An instruction 38 is displayed at step 104 to align the hub device to the patient 4, and specifically to the portion of the patient containing the position sensor 10 that is being calibrated. Again, such instruction 38 can be displayed on a display device 55 incorporated into or associated with the hub device 200. Such instruction 38 may be textual and/or pictorial instructions. Alternatively or additionally, the instructions provided at steps 102 and 104 may be audio instructions provided by audio output devices associated with the hub device 200. Instructions are then executed at step 106 to control the display device 55 to display a calibration record input option. For example, where the display device 55 is a touchscreen, a button or other location indicator can be displayed with instructions for the clinician to touch that area of the display device 55 when the hub device 200 is aligned with the relevant portion of the patient 4. Additionally, the display may be controlled to provide instruction 38 to a user on how to input the calibration record command, such as by pressing a button or other touch input element comprising part of the user interface 210 on the hub device 200.

The input command 40 to record the calibration position measurement is then received at step 108 once the clinician provides the input requested at step 106. A position measurement is received from the calibration position sensor 20 and is recorded as the first calibration position measurement at step 110. The calibration position measurement is recorded while the hub device 200 is aligned with the portion of the patient 4 containing the position sensors 10 being calibrated. Depending on the configuration of the patient monitoring system 1, including the type of position sensor 10, the calibration process may require that the hub device 200 be aligned with the patient while the patient assumes a predetermined calibration position. Alternatively, the calibration process may not require a predetermined calibration position, and the hub device 200 can be aligned with the relevant portion of the patient 4 in whatever position the patient happens to be in, which can be known to and determined by the position analysis module 52 based on the position measurement data from the calibration position sensor 20, which is calibrated to the known zeroed position 42 coordinates. Simultaneously, or approximately at the same time, a patient position measurement from the first position sensor 10 is recorded as the first patient position measurement at step 112, which will correspond to and be compared to the first calibration position measurement recorded at step 110. Step 113 is then executed to correlate the position measurements—e.g., calculate a difference between the first calibration position measurement and the first patient position measurement, which is then used at step 114 to determine the calibration map.

FIG. 7 depicts another embodiment of the method 100 including differing calibration steps. In this calibration portion of the method 100, an instruction 38 is provided at step 101 to align the hub device to the relevant portion of the patient 4 containing the position sensor 10 to be calibrated. As described above, such instruction 38 may be a visual instruction provided on the display 55 of the hub device 200, and/or it may include an audio instruction provided by an audio output device associated with the system 1. Similarly, an instruction is provided at step 103 instructing that the patient execute a predefined movement, such as a transition from supine to a seated position, as described above. The predefined movement may be any predefined movement of the patient that can help identify axes of the position sensor 10 being calibrated, so that the position measurement data therefrom can be calibrated to the position measurement data from the calibration position sensor 20. Accordingly, two or more calibration position measurements are recorded at step 110 during the predefined movement, while the hub device is moved in a way that mimics the patient movement. Meanwhile, position measurement data is received from the position sensor 10 during the movement, and step 112 is executed to identify corresponding patient position measurements in that data that occurred at the same time, or at least very close to the same time, as the calibration position measurements. Step 113a is determined to correlate relevant axes between the patient position measurements and the calibration position measurements. As described above, multiple position measurements may need to be taken during the calibration process in order to identify all three axes of the position sensor 10 with the needed degree of certainty. For example, the number of calibration measurements and steps needed may be dictated by the type of position sensor employed in the system 1, which is described in detail above. Step 113b determines whether all axes have been correlated. If not, then the foregoing calibration steps are repeated using a different predefined movement for the patient based on which axes remain undetermined. Once all axes have been identified, the patient position measurements compared to the calibration position measurements to determine the calibration map at step 114.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A method of measuring patient position by a patient monitoring system, the method comprising:
   providing a first position sensor attachable to a portion of a patient, wherein the position sensor includes at least one of an accelerometer and a gyroscope;
   providing a hub device that includes a calibration position sensor;
   moving the hub device into alignment with the portion of the patient to which the first position sensor is attached;
   measuring a first calibration position with the calibration position sensor while the hub device is aligned with the portion of the patient where the first position sensor is attached;
   measuring a first patient position measurement with the first position sensor;
   determining a difference between the first calibration position measurement and the first patient position measurement; and
   determining a calibration map for the first position sensor based on the difference to define position measurements from the first position sensor and position measurements from the calibration position sensor with respect to a common set of axes.

2. The method of claim 1, further comprising:
   receiving subsequent position measurement data from the first position sensor; and
   determining a patient position based on the calibration map and the position measurement data.

3. The method of claim 1, further comprising:
   displaying an instruction on a display of the hub device to align the hub device with the portion of the patient where the first position sensor is attached; and
   receiving an input command to record the first calibration position measurement after the hub device is moved into alignment with the portion of the patient to which the first position sensor is attached.

4. The method of claim 3, further comprising displaying an instruction on the display of the hub device that the patient assume a first calibration position prior to aligning the hub device with the portion of the patient where the first position sensor is attached.

5. The method of claim 4, further comprising:
   instructing that the patient assume a second calibration position;
   displaying a second instruction to align the hub device with the portion of the patient where the first position sensor is attached;
   receiving an input command to record a second calibration position measurement;
   receiving the second calibration position measurement from the calibration position sensor;
   receiving the second patient position measurement from the first position sensor; and
   wherein the calibration map for the first position sensor is further determined based on a difference between the second calibration position measurement and the second patient position measurement.

6. The method of claim 3, further comprising:
   providing a second position sensor attachable to a different portion of the patient that the first position sensor;

displaying a second instruction to align the hub device with the portion of the patient where the second position sensor is attached;

receiving an input command to record a second calibration position measurement;

receiving the second calibration position measurement from the calibration position sensor;

receiving a second position measurement from the second position sensor; and determining a calibration map for the second position sensor based on a difference between the second calibration position measurement and the second position measurement.

7. The method of claim 1, further comprising:

displaying an instruction on a display of the hub device to align the hub device with the portion of the patient where the first position sensor is attached while the patient makes a predefined movement;

recording at least two calibration position measurements while the patient is moving;

receiving at least two position measurements sensed with the first position sensor while the patient was moving; and wherein the calibration map for the first position sensor is determined based on a difference between the at least two calibration position measurements and the at least two position measurements.

8. A patient monitoring system comprising:

a first position sensor attachable to a portion of a patient;

a hub device including a calibration position sensor;

wherein the first position sensor and the calibration position sensor each include at least one of an accelerometer and a gyroscope;

a processor;

a position analysis module executable on the processor to:
receive a first calibration position measurement from the calibration position sensor while the hub device is aligned with the portion of the patient where the first position sensor is attached;
receive a first patient position measurement from the first position sensor;
determine a difference between the first calibration position measurement and the first patient position measurement; and
determine a calibration map for the first position sensor based on the difference so as to define position measurements from the first position sensor and position measurements from the calibration position sensor with respect to a common set of axes.

9. The patient monitoring system of claim 8, wherein the position analysis module is further executable on the processor to:
receive subsequent position measurement data from the first position sensor; and
determine a patient position based on the calibration map and the position measurement data.

10. The patient monitoring system of claim 8, wherein each position sensor further includes a magnetometer.

11. The patient monitoring system of claim 8, wherein the processor and the position analysis module are in the hub device.

12. The patient monitoring system of claim 8, wherein the first position sensor is in a physiological data acquisition device attachable to the patient and configured to acquire physiological data from the patient.

13. The patient monitoring system of claim 8, wherein the position analysis module is further executable on the processor to:
display on a display of the hub device a first instruction to align the hub device with the portion of the patient where the first position sensor is attached; and
receive an input command to record the first calibration position measurement.

14. The patient monitoring system of claim 13, wherein the position analysis module is further executable on the processor to instruct that the patient assume a first calibration position in conjunction with the instruction to align the hub device with the portion of the patient where the first position sensor is attached.

15. The patient monitoring system of claim 14, wherein the position analysis module is further executable on the processor to:
instruct that the patient assume a second calibration position;
display a second instruction to align the hub device with the portion of the patient where the first position sensor is attached;
receive an input command to record a second calibration position measurement;
record the second calibration position measurement from the calibration position sensor;
receive a second patient position measurement; and
wherein the calibration map for the first position sensor is further determined based on a difference between the second calibration position measurement and the second patient position measurement.

16. The patient monitoring system of claim 13, wherein the system further includes a second position sensor attachable to the patient, and wherein the position analysis module is further executable on the processor to:
display a second instruction to align the hub device with the portion of the patient where the second position sensor is attached;
receive an input command to record a second calibration position measurement;
record the second calibration position measurement from the calibration position sensor;
receive a second position measurement from the second position sensor; and
determine a calibration map for the second position sensor based on a difference between the second calibration position measurement and the second position measurement.

17. A method of calibrating position measurement by a patient monitoring system, the method comprising:
attaching a first position sensor to a patient;
aligning a hub device with a portion of the patient where the first position sensor is attached when the patient is in a first position, the hub device including a calibration position sensor, wherein the first position sensor includes at least one of an accelerometer and a gyroscope;
providing an input command via a user interface associated with the hub device to record a first calibration position measurement;
recording a first calibration position measurement from the calibration position sensor;
recording a first patient position measurement from the first position sensor;
determine a difference between the first calibration position measurement and the first patient position measurement; and determining a calibration map for the first position sensor based on the difference to define position measurements from the first position sensor and position measurements from the calibration position sensor with respect to a common set of axes.

18. The method of claim 17, further comprising:

aligning a hub device with the portion of the patient where the first position sensor is attached when the patient is in a second position;

providing a second input command via a user interface on the hub device to record a second calibration position measurement;

recording the second calibration position measurement from the calibration position sensor;

receiving a second patient position measurement from the first position sensor; and determining a calibration map for the first position sensor further based on a difference between the second calibration position measurement and the second patient position measurement.

19. The method of claim 17, further comprising aligning the hub device with the portion of the patient while the patient makes a predefined movement;

recording at least two calibration position measurements from the calibration position sensor while the patient is moving;

receiving at least two position measurements sensed with the first position sensor while the patient was moving; and wherein the calibration map for the first position sensor is further determined based on a difference between the at least two calibration position measurements and the at least two position measurements.

* * * * *